(12) United States Patent
Ladva

(10) Patent No.: US 9,232,854 B2
(45) Date of Patent: Jan. 12, 2016

(54) ORAL HYGIENE TOOL

(71) Applicant: Suresh Kurji Ladva, Brea, CA (US)

(72) Inventor: Suresh Kurji Ladva, Brea, CA (US)

( * ) Notice: Subject to any disclaimer, the term of this patent is extended or adjusted under 35 U.S.C. 154(b) by 0 days.

(21) Appl. No.: 14/492,812

(22) Filed: Sep. 22, 2014

(65) Prior Publication Data

US 2015/0007402 A1   Jan. 8, 2015

Related U.S. Application Data

(63) Continuation-in-part of application No. 14/305,549, filed on Jun. 16, 2014, now Pat. No. 9,055,809.

(60) Provisional application No. 61/923,206, filed on Jan. 2, 2014.

(51) Int. Cl.
*A46B 15/00* (2006.01)
*A61B 17/24* (2006.01)

(52) U.S. Cl.
CPC ............ *A46B 15/0081* (2013.01); *A61B 17/244* (2013.01); *A46B 2200/1066* (2013.01)

(58) Field of Classification Search
CPC .. A46B 5/005; A46B 15/0081; A61B 17/244; B25G 1/04
USPC ......... 15/111, 144.3, 144.4; 16/429; 606/161; D4/108; D24/147
See application file for complete search history.

(56) References Cited

U.S. PATENT DOCUMENTS

| | | | | |
|---|---|---|---|---|
| 1,495,675 A * | 5/1924 | Colt | ............................... | 132/309 |
| 1,728,956 A | 9/1929 | Darmitzel | | |
| 2,574,654 A * | 11/1951 | Moore | .......................... | 606/161 |
| 2,651,068 A | 9/1953 | Seko | | |
| 3,931,968 A * | 1/1976 | Hedberg | ........................ | 473/552 |
| 4,455,704 A * | 6/1984 | Williams | ......................... | 15/111 |
| 5,980,541 A | 11/1999 | Tenzer | | |
| D508,325 S | 8/2005 | Zunga | | |
| D515,817 S | 2/2006 | Siemer | | |
| 7,434,495 B2 * | 10/2008 | Lin | ............................... | 81/177.2 |
| 2008/0307595 A1* | 12/2008 | Zielinski | ...................... | 15/144.4 |
| 2009/0235474 A1* | 9/2009 | Seigel | ........................... | 15/111 |

* cited by examiner

*Primary Examiner* — Mark Spisich

(74) *Attorney, Agent, or Firm* — Eric Karich; Karich & Associates

(57) ABSTRACT

A oral hygiene tool has a tongue scraper and a toothbrush with an elongate toothbrush body. The tongue scraper is telescopically engaged with the elongate toothbrush body of the toothbrush, so that the tongue scraper can move between a collapsed configuration and an extended configuration relative to the toothbrush. A locking system may be included for locking the tongue scraper with the toothbrush so that relative movement is prohibited, and a resilient wall may cover and seal each of the locking apertures.

4 Claims, 6 Drawing Sheets

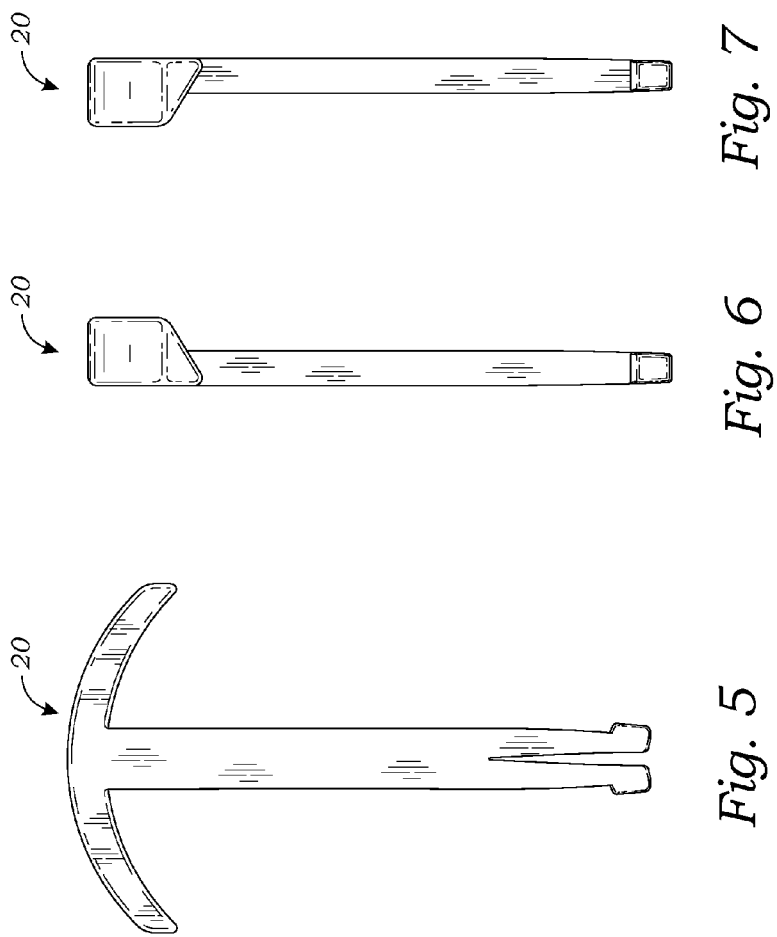

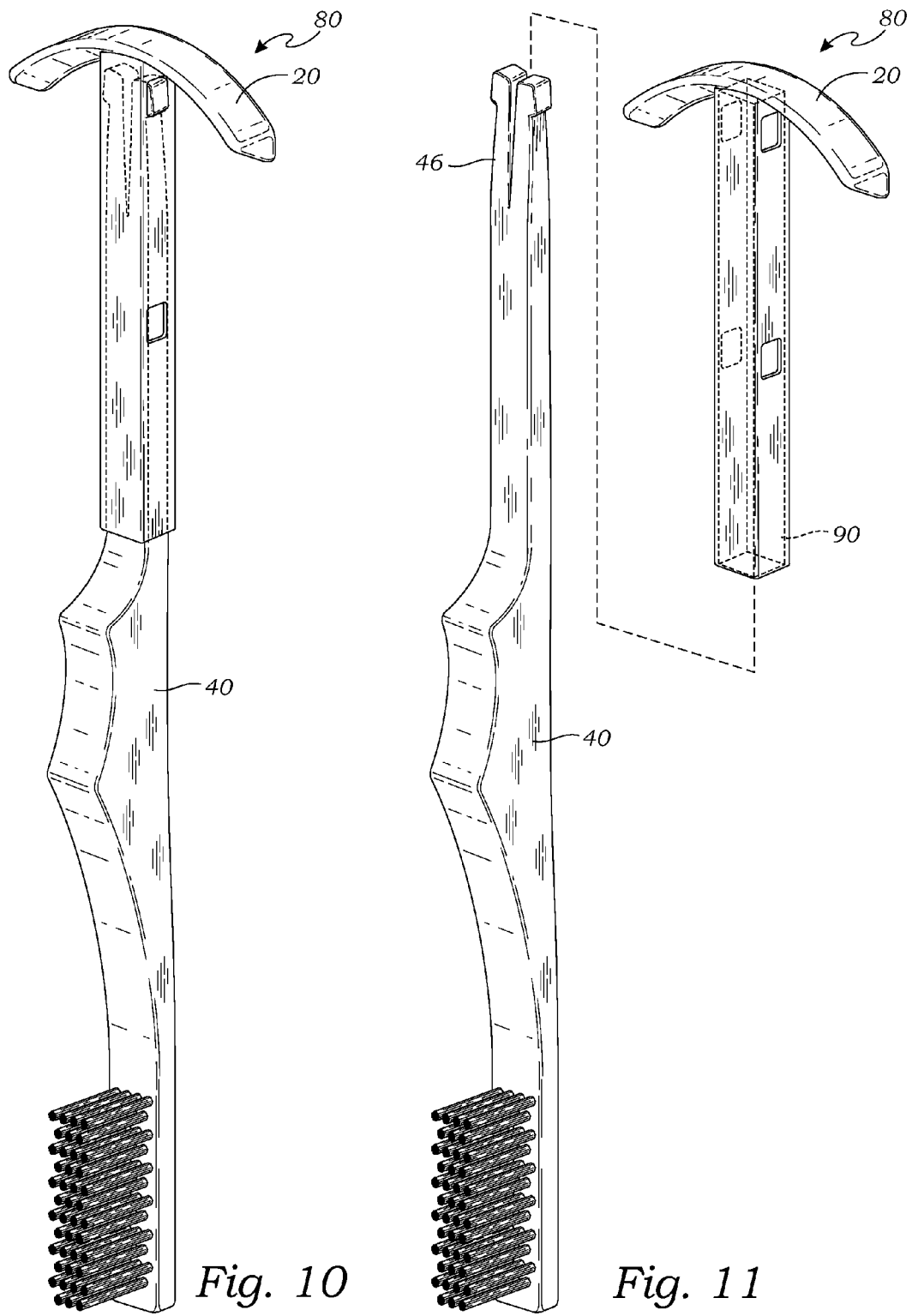

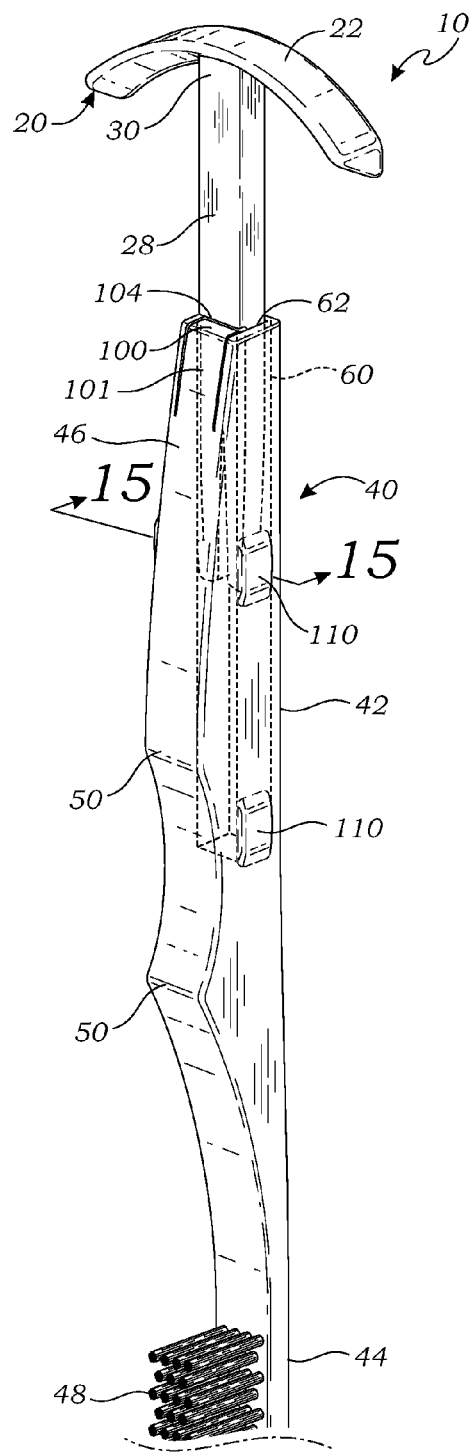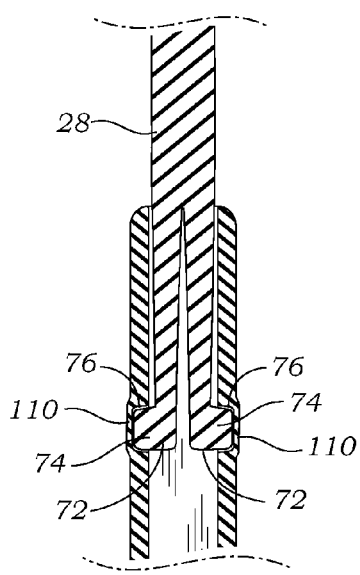
Fig. 14
Fig. 15

ORAL HYGIENE TOOL

CROSS-REFERENCE TO RELATED APPLICATIONS

This application for a utility patent is a continuation-in-part of a previously filed utility patent, having the application Ser. No. 14/305,549, filed Jun. 16, 2014, now U.S. Pat. No. 9,055,809.

This application for a utility patent also claims the benefit of U.S. Provisional Application No. 61/923,206, filed Jan. 2, 2014.

BACKGROUND OF THE INVENTION

1. Field of the Invention

This invention relates generally to oral hygiene tools, and more particularly to a tool that includes both a toothbrush and a tongue scraper.

2. Description of Related Art

Tongue scrapers and toothbrushes are common oral hygiene products. The prior art teaches a simple combination of the two tools; however, the resulting device is unwieldy, and is either to short to use, or too long to store. The present invention addresses those needs by providing a novel and efficient tongue scraper that telescopically engages a toothbrush.

The prior art teaches toothbrushes, tongue scrapers, and the combination of tooth brushes and tongue scrapers. However, the prior art does not teach such a combination with a tongue scraper that telescopically engages a toothbrush, including a locking mechanism for locking the tongue scraper in either a collapsed configuration or an extended configuration. The present invention fulfills these needs and provides further advantages as described in the following summary.

SUMMARY OF THE INVENTION

The present invention teaches certain benefits in construction and use which give rise to the objectives described below.

The present invention provides a oral hygiene tool for scraping a tongue and brushing teeth. The oral hygiene tool has a tongue scraper with an elongate scraper body having an elongate upper edge forming a scraping surface for the tongue, and an elongate connector body having a first end and a second end, the elongate scraper body being connected to the first end transverse to the elongate connector body. The oral hygiene tool also includes a toothbrush with an elongate toothbrush body having a proximal end and a distal end, a plurality of brushes extending from the proximal end of the elongate toothbrush body. The elongate connector body of the tongue scraper is telescopically engaged with the elongate toothbrush body of the toothbrush, so that the tongue scraper can move between a collapsed configuration and an extended configuration relative to the toothbrush.

In one embodiment, the oral hygiene tool further includes a locking system for locking the tongue scraper with the toothbrush so that relative movement is prohibited. The locking system may include an inwardly extending flange that can move between a locking position and an unlocking position, a biasing mechanism for biasing the inwardly extending flange towards the unlocking position, and a groove formed for receiving the inwardly extending flange when moved to the locking position.

In another embodiment, the oral hygiene tool further includes a resilient wall covering and sealing each of the locking apertures so that when the at least one locking prong engages one of the locking apertures, the locking prong may be disengaged from the locking aperture by pressing inwardly on the resilient wall.

A primary objective of the present invention is to provide an oral hygiene tool having advantages not taught by the prior art.

Another objective is to provide an oral hygiene tool with a tongue scraper that telescopically engages a toothbrush.

Another objective is to provide an oral hygiene tool with a locking system for locking the tongue scraper in a given position for use of the tongue scraper.

A further objective is to provide an oral hygiene tool that includes resilient walls covering each of the locking apertures of the toothbrush.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 4 is a front elevational view of a tongue scraper of the oral hygiene tool;

FIG. 5 is a rear elevational view thereof;

FIG. 6 is a left elevational view thereof;

FIG. 7 is a right elevational view thereof;

FIG. 8 is a top plan view thereof;

FIG. 9 is a bottom plan view thereof;

FIG. 10 is a perspective view of the oral hygiene tool in the collapsed configuration, according to another embodiment of the present invention, illustrating the tongue scraper having the elongate inner chamber;

FIG. 11 is a perspective view of the oral hygiene tool, illustrating the oral hygiene tool in a disengaged configuration;

FIG. 14 is a perspective view of the oral hygiene tool of FIG. 12, illustrating resilient walls covering each of the locking apertures of the toothbrush; and FIG. 15 is a sectional view thereof taken along line 15-15 in FIG. 14.

DETAILED DESCRIPTION OF THE INVENTION

The above-described drawing figures illustrate the invention, an oral hygiene tool 10 for scraping a tongue and brushing teeth. The oral hygiene tool 10 combines a tongue scraper 20 and a toothbrush 40 that engage each other in an extendable, or telescoping, relationship.

Figure 1:
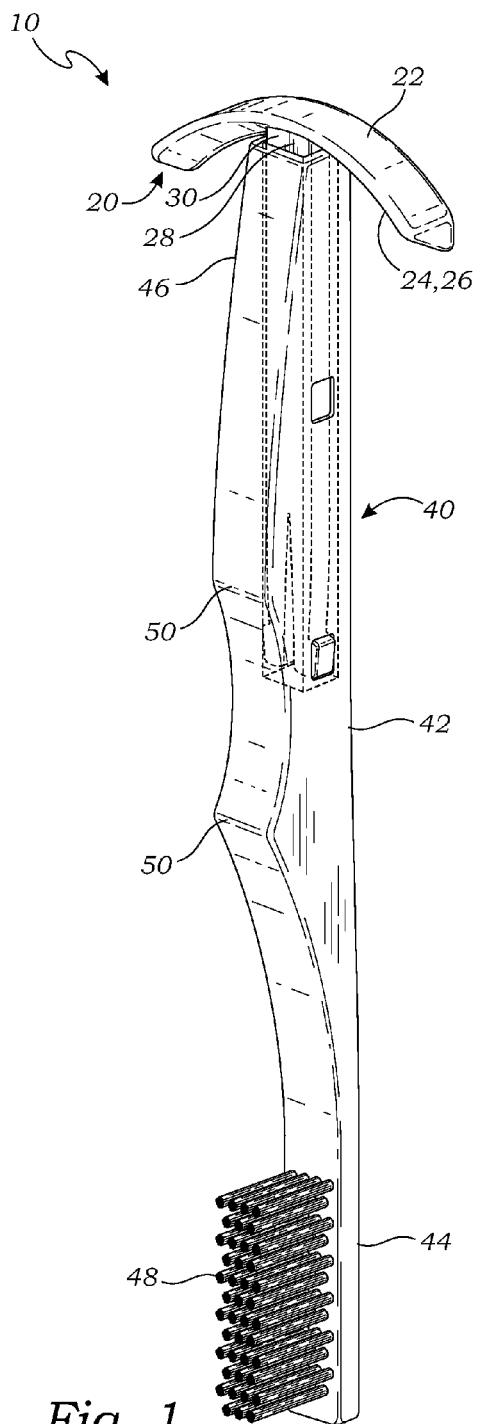
FIG. 1 is a perspective view of an oral hygiene tool, in a collapsed configuration, according to one embodiment of the present invention.
Figure 2:
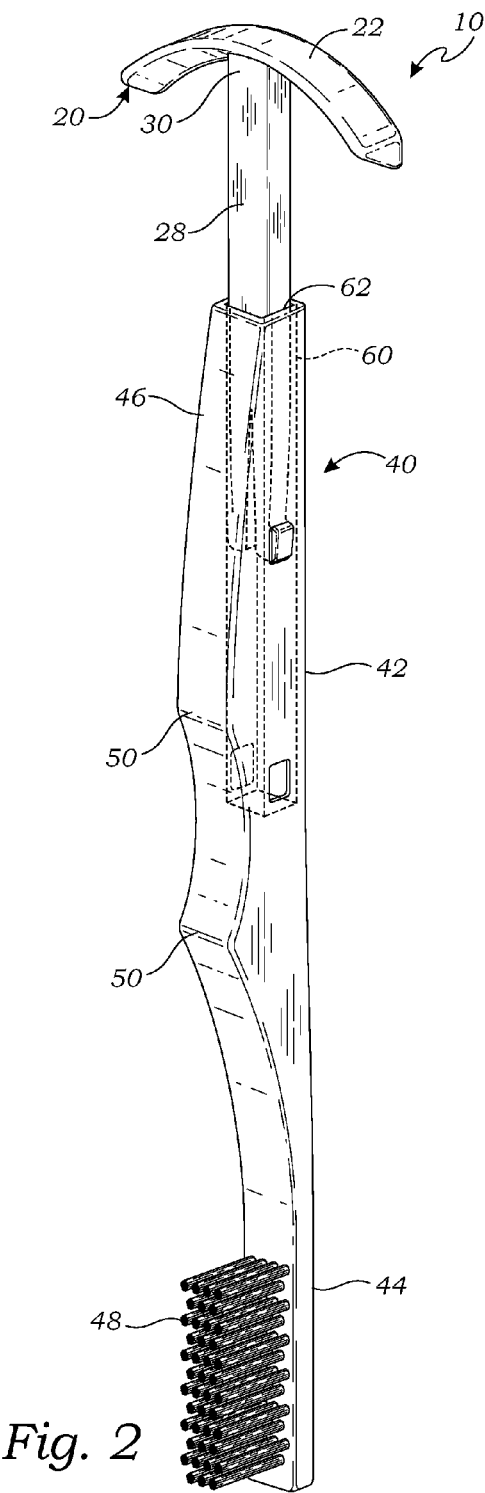
FIG. 2 is a perspective view of the oral hygiene tool in an extended configuration.
Figure 3:
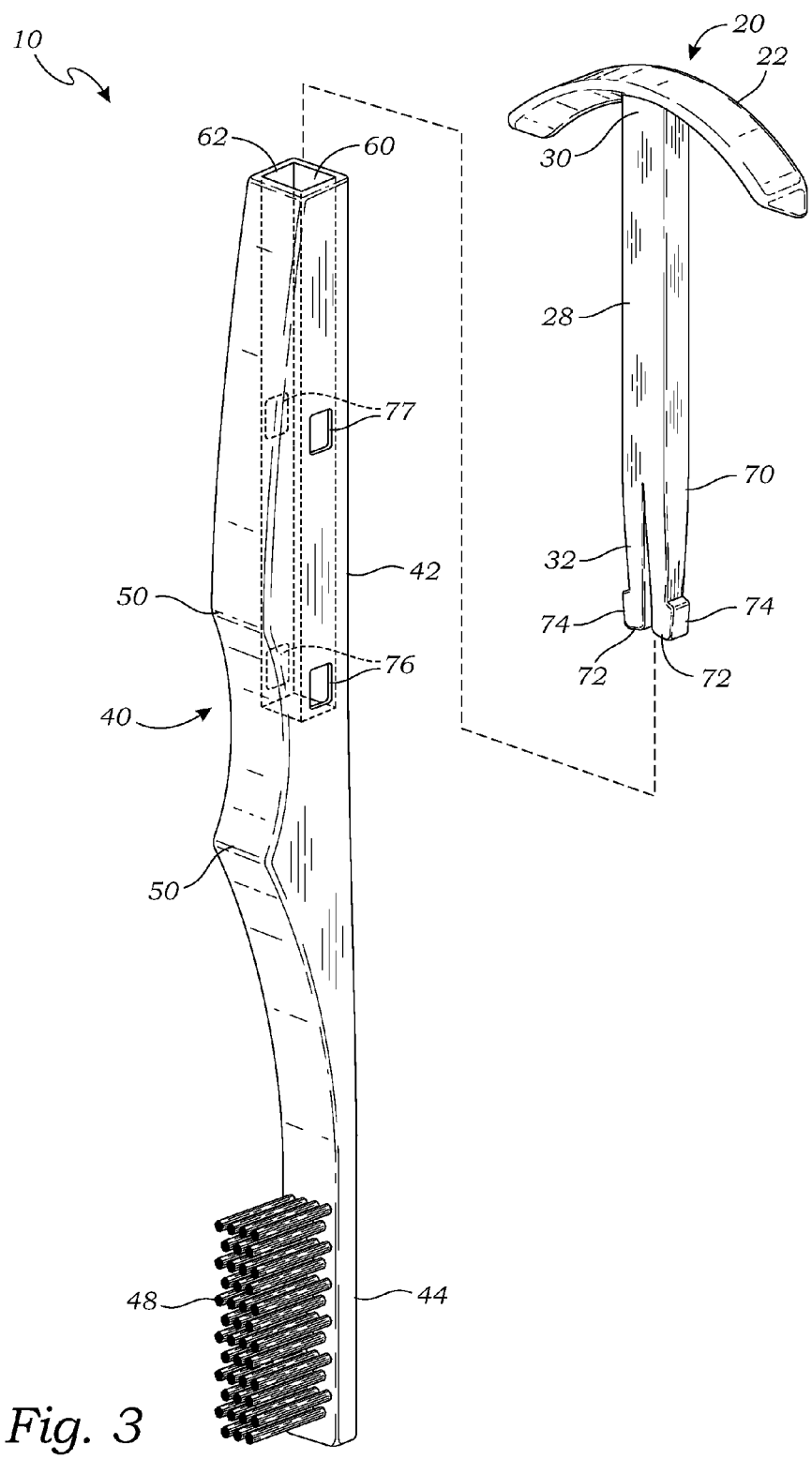
FIG. 3 is a perspective view of the oral hygiene tool in a disengaged configuration.

FIG. 1 is a perspective view of the oral hygiene tool 10 in a collapsed configuration, FIG. 2 is a perspective view of the oral hygiene tool 10 in an extended configuration, and FIG. 3 is a perspective view of the oral hygiene tool 10 in a disengaged configuration. As illustrated in FIGS. 1-3, the tongue scraper 20 includes an elongate scraper body 22 and an elongate connector body 28. The elongate scraper body 22 extends laterally on either side of and generally traverse to the elongate connector body 28, and includes an elongate upper edge 24 that is shaped for scraping the tongue. In the present embodiment, the elongate scraper body 22 is curved and has an upwardly extending wedge-shaped cross section that narrows to the elongate upper edge 24. In other embodiments, the elongate scraper body 22 may have an alternative structure with any shape known to one skilled in the art for scraping the tongue, and such alternatives should be considered within the scope of the present invention.

As illustrated in FIGS. 1-3, the elongate connector body 28 of the tongue scraper 20 has a first end 30 and a second end 32. The first end 30 is connected with the elongate scraper body 22. The second end 32 extends outwardly for engaging the toothbrush 40 in a telescoping manner. In the embodiment of FIGS. 1-3, the elongate connector body 28 is a post shaped as an elongate cuboid. In alternate embodiments the elongate connector body 28 may be a structure with any desired shape, e.g. a bar, rod, wedge, or other shape desired by one skilled in the art. In other embodiments, the elongate connector body 28 may have a tapered section (not shown) where the elongate connector body 28 connects to the elongate scraper body 22 so as either not to obstruct, or reduce the obstruction of, the portion of the elongate scraper body 22 that is in contact with the tongue during use. While FIG. 1 illustrates one embodiment of the elongate connector body 28, those skilled in the art may devise alternative embodiments, and these alternative or equivalent are considered within the scope of the present invention.

As illustrated in FIGS. 1-3, the toothbrush 40 has an elongate toothbrush body 42 which may be used as a handle for the toothbrush 40, and which telescopically engages the elongate connector body 28 of the tongue scraper 20. The elongate toothbrush body 42 may have a proximal end 44, a distal end 46, and brushes 48 extending from the proximal end 44 of the elongate toothbrush body 42. The proximal end 44 of the toothbrush 40 is the end of the toothbrush 40 which is inserted into the mouth during use.

As illustrated in FIGS. 1-3, the elongate toothbrush body 42 may also include a plurality of raised sections 50 to aid in the grasping and use of the oral hygiene tool 10, creating an ergonomically suitable handle. The presence of the raised sections 50 may create depressions which conform to functions described above, e.g. providing an ergonomic handle for use, or any other functions desired by one skilled in the art. In alternate embodiments, the raised sections 50 and the depressions may be varied in shape and design to serve any function e.g. providing a gentle or comfortable surface, providing ridges to prevent slippage, providing features such as clasps or releases for storing the oral hygiene tool 10, or any other features desired by one skilled in the art.

The distal end 46 is the end of the elongate toothbrush body 42 which telescopically engages the elongate connector body 28 of the tongue scraper 20. In the embodiment of FIGS. 1-3, the distal end 46 includes an elongate inner chamber 60 shaped to receive the second end 32 of the elongate connector body 28, via a chamber aperture 62. The elongate connector body 28 and the elongate toothbrush body 42 may then telescopically engage each other.

The telescoping construction of the present invention allows several configurations where the length of the oral hygiene tool 10 may be varied according to the needs of the user. In the present embodiment, shown in FIGS. 1-3, the elongate connector body 28 of the tongue scraper 20 may be telescopically engaged with the elongate toothbrush body 42 of the toothbrush 40, so that the tongue scraper 20 can move between a collapsed configuration and an extended configuration relative to the toothbrush 40. In alternate embodiments, the telescoping of the tongue scraper 20 may be accomplished by a variety of means, e.g. interlocking bodies, tracks, extensions, or any methods desired by one skilled in the art.

As shown in the embodiment of FIGS. 1-3, the elongate inner chamber 60 is within the elongate toothbrush body 42. The inner chamber may have the chamber aperture 62 at the distal end 46 for allowing the elongate connector body 28 to be inserted into the elongate inner chamber 60. The elongate inner chamber 60 may be shaped to allow the elongate connector body 28 of the tongue scraper 20 to telescopically engage the elongate toothbrush body 42.

The elongate inner chamber 60 may have any shape which allows the elongate connector body 28 to telescopically engage with the elongate toothbrush body 42. A square cross-sectional shape, as shown, prevents relative rotation, but in alternative embodiments other cross-sectional shapes may be used. The elongate inner chamber 60 may extend any length longitudinally along the elongate toothbrush body 42. As shown in the embodiment of FIG. 1, one definition of the collapsed configuration may be when the elongate inner chamber 60 is located within the elongate toothbrush body 42 and the elongate connector body 28 is substantially inside the elongate toothbrush body 42. While FIGS. 1-3 illustrate one embodiment of the elongate inner chamber 60, those skilled in the art may devise alternative embodiments, and these alternative or equivalent are considered within the scope of the present invention.

As shown in FIGS. 1-3, the telescoping construction of the oral hygiene tool 10 allows the extended configuration in addition to the collapsed configuration. As shown in FIG. 2, one definition of the extended configuration may be when the elongate inner chamber 60 is located within the elongate toothbrush body 42 and the elongate connector body 28 is substantially, though not completely, outside the elongate toothbrush body 42.

As shown in FIG. 3, the telescopic construction of the oral hygiene tool 10 may allow for the toothbrush 40 and the tongue scraper 20 to be physically separated, which may be defined as the disengaged configuration. In such a configuration, the toothbrush 40 and/or the tongue scraper 20 may be used separately, if desired by a user. In one embodiment, the act of disengagement is reversible, allowing the tongue scraper 20 and the toothbrush 40 to be reassembled. Reassembly may be done by inserting the second end 32 of the tongue scraper 20 through the chamber aperture 62 of the elongate inner chamber 60, thereby re-engaging the tongue scraper 20 and the toothbrush 40. The ability of the oral hygiene tool 10 to be connected together into a single tool which is compact in size enables the oral hygiene tool 10 to be easily transported, stored, and also used while traveling.

As shown in FIG. 3, the oral hygiene tool 10 may further include a locking mechanism 70 for locking the position of the tongue scraper 20 with respect to the toothbrush 40. In the embodiment of FIG. 3, the locking mechanism 70 includes locking apertures 76 and 77, and resilient arms 72 with locking prongs 74 which removably engage the locking apertures 76 and 77 for releasably locking the tongue scraper 20 with respect to the toothbrush 40.

In the present embodiment, there are a first pair of locking apertures 77 located closest to the distal end 46 of the toothbrush 40, and a second pair of locking apertures 76 located between the first pair of locking apertures 77 and the proximal end 44 of the toothbrush 40. The first pair of locking apertures 77 are longitudinally separated and azimuthally aligned with the second pair of locking apertures 76. When the elongate connector body 28 is positioned such that the first pair of locking apertures 77 are engaged, the oral hygiene tool 10 is in the extended position. When the elongate connector body 28 is positioned such that the second pair of locking aperture 76 are engaged, the oral hygiene tool 10 is in the collapsed position. While FIG. 3 illustrates one embodiment of the locking apertures 76 and 77, those skilled in the art may devise alternative embodiments, and these alternative or equivalent are considered within the scope of the present invention.

The resilient arms 72 extend from the elongate connector body 28, and is flexible enough to allow some movement of the resilient arm 72, and in particular, allow a radial deflection which increases towards the second end 32 and which effectively narrows the effective diameter or area of the second end 32. In alternate embodiments, the resilient arm 72 may be constructed differently, e.g. a compressible arm (as opposed to a deflecting arm), or any other sort of resilient arm 72 desired by one skilled in the art. In the present embodiment, there is a pair of the resilient arms 72, each resilient arm 72 being opposite one another azimuthally on the elongate connector body 28. In alternate embodiments, there may be any number of, and orientation of, the resilient arms 72 as desired by one skilled in the art.

The present embodiment may have a locking prong 74 extending radially from the resilient arm 72. In the present embodiment, the locking prong 74 is a protrusion shaped to removably and lockingly engage the locking apertures 76 and 77.

The resilient arm 72 may be pressed away from the locking apertures 76 and 77 to disengage the locking mechanism 70 and allow the elongate connector body 28 to slide longitudinally relative to the connector body 28. In the present embodiment, the locking arm is angled relative to the longitudinal axis such that when a longitudinal force is applied, there is an inward force on the resilient arms 72. If the inward force on the resilient arm 72 is sufficient to deflect the resilient arm 72 inward at the location of the locking prong 74, such that the locking prong 74 disengages from the locking apertures 76 and 77, the locking mechanism 70 will becomes disengaged and allow the telescoping motion of the toothbrush 40 and the tongue scraper 20. The term "locking prong" and "locking aperture" are both hereby defined to include any form of interlocking element and receiver (hole, aperture, bore, etc.) that can interlock as shown. In alternate embodiments, other means for engaging/disengaging may be used, e.g. releases, springs, catches, tracks, compression fittings, or any other means desired by one skilled in the art.

FIG. 4 is a front elevational view of the tongue scraper 20, and FIGS. 5-9 are rear, left, and right elevational views, and top and bottom views, of the tongue scraper 20.

FIGS. 10 and 11 are perspective views of a second embodiment of the oral hygiene tool 80. In this embodiment, the male/female relationship between the toothbrush and the tongue scraper 20 may be reversed. In the embodiment of FIGS. 10-11, the elongate connector body 28 of the tongue scraper 20 may include an elongate inner chamber 90 (that is similar to the chamber 60 of FIGS. 1-3), and the distal end 46 of the toothbrush 40 telescopically engages the elongate inner chamber 90.

Figures 12, 13:
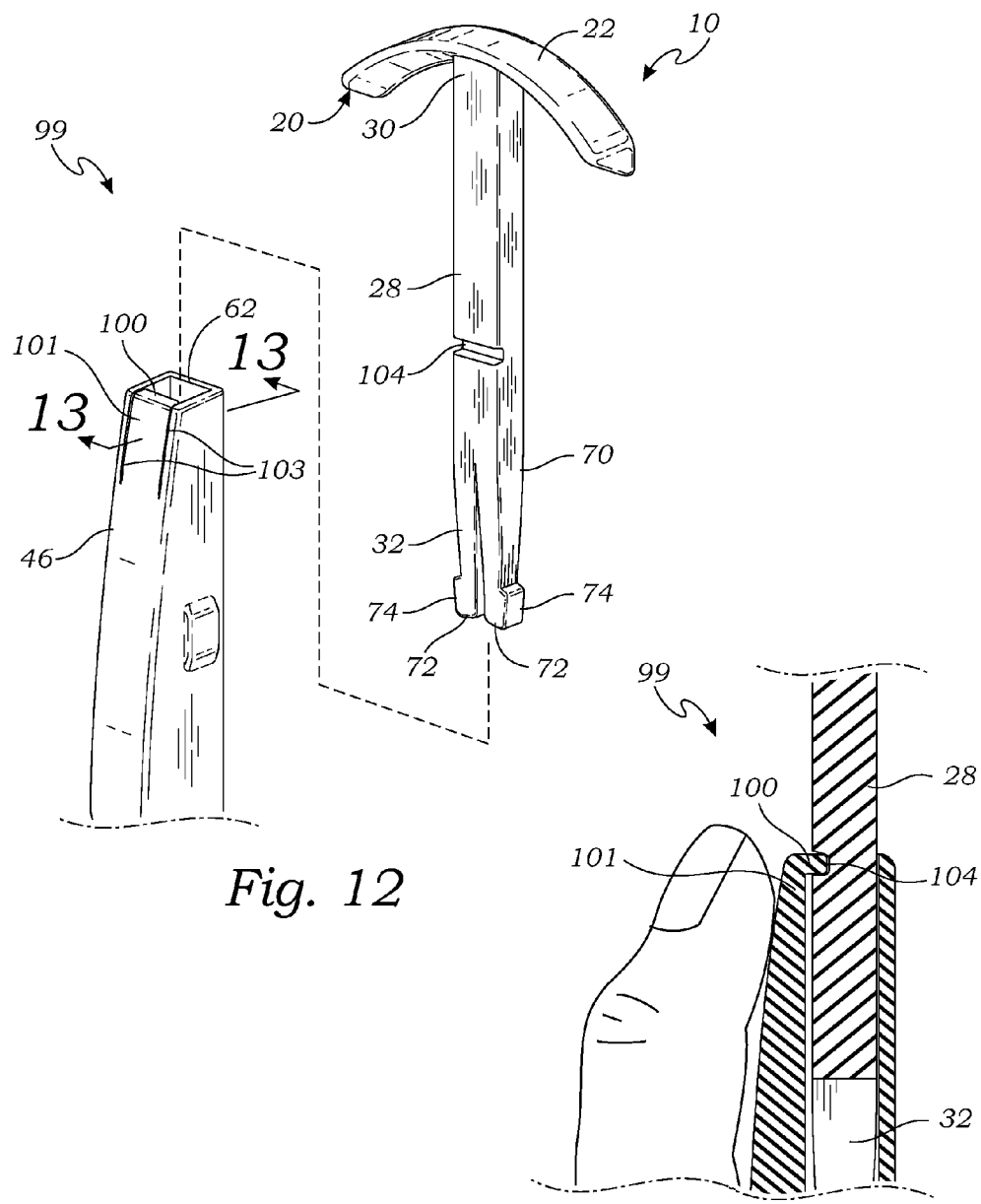
FIG. 12 is an exploded perspective view of a second embodiment of the oral hygiene tool, illustrating a locking system that can be used to lock the tongue scraper into a given position relative to the toothbrush.
FIG. 13 is a sectional view thereof taken along line 13-13 in FIG. 12.

FIG. 12 is an exploded perspective view of a second embodiment of the oral hygiene tool 10. FIG. 13 is a sectional view thereof taken along line 13-13 in FIG. 12. As shown in FIGS. 12 and 13, the oral hygiene tool 10 may further include a locking system 99 that can be used to lock the tongue scraper 20 into a given position relative to the toothbrush 40.

In this embodiment, the locking system 99 includes an inwardly extending flange 100 that can move between a locking position and an unlocking position. The locking system 99 may include a biasing mechanism 101 for biasing the inwardly extending flange 100 towards the unlocking position, and a groove 104 formed for receiving the inwardly extending flange 100 when moved to the locking position.

In this embodiment, the biasing mechanism 101 is a resilient hinge that pivotally mounts the inwardly extending flange 100 on the toothbrush, and is biased towards the unlocking position, although this could be reversed. Also in this embodiment, the groove 104 traverses the elongate connector body 28 of the tongue scraper 20. The resilient hinge 101 may be separated from the toothbrush by a pair of slots 103, as shown, or formed in another manner.

FIG. 14 is a perspective view of the oral hygiene tool 10 of FIG. 12, illustrating resilient walls 110 covering each of the locking apertures 76 (shown as reference numbers 76 and 77 in FIG. 3) of the toothbrush. FIG. 15 is a sectional view thereof taken along line 15-15 in FIG. 14.

As shown in FIGS. 14 and 15, the resilient walls 110 cover and seal each of the locking apertures 76 and 77 (as shown in FIG. 3) so that contaminants cannot enter the elongate inner chamber 60 of the toothbrush 40. The resilient walls 110 are resilient, however, so that when the at least one locking prong 74 is engaged in one of the locking apertures 76, the locking prong 74 may be pressed inwardly and disengaged from the locking aperture 76 and 77 by pressing inwardly on the resilient wall 110.

As used in this application, the term "longitudinally" is taken to be the direction along an axis extending through the elongate connector body and the elongate toothbrush body. The longitudinal direction may then be defined by the direction of the telescoping motion of the elongate connector body and the elongate toothbrush body, described throughout the application. The term "azimuthally" is then the azimuthal or polar coordinate around the axis. The term "radially" is then the radial direction from the axis.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A oral hygiene tool for scraping a tongue and brushing teeth, the oral hygiene tool comprising:
   a tongue scraper comprising an elongate scraper body having an elongate upper edge forming a scraping surface for the tongue, and an elongate connector body having a first end and a second end, the elongate scraper body being connected to the first end transverse to the elongate connector body;
   a toothbrush comprising an elongate toothbrush body having a proximal end and a distal end, and a plurality of brushes extending from the proximal end;
   the elongate connector body of the tongue scraper being telescopically engaged with the elongate toothbrush body of the toothbrush, so that the tongue scraper can move between a collapsed configuration and an extended configuration relative to the toothbrush; and a locking system for locking the tongue scraper with the toothbrush so that relative movement is prohibited, wherein the locking system includes an inwardly extending flange that can move between a locking position and an unlocking position, a biasing mechanism for biasing the inwardly extending flange towards the unlocking position, and a groove formed for receiving the inwardly extending flange when moved to the locking position.

2. The oral hygiene tool of claim 1, wherein the locking system comprises a resilient hinge that pivotally mounts the inwardly extending flange on the toothbrush, and wherein the groove traverses the elongate connector body of the tongue scraper.

3. The oral hygiene tool of claim 2, wherein the resilient hinge is separated from the toothbrush by a pair of slots.

4. A oral hygiene tool for scraping a tongue and brushing teeth, the oral hygiene tool comprising:

a tongue scraper comprising an elongate scraper body having an elongate upper edge forming a scraping surface for the tongue, and an elongate connector body having a first end and a second end, the elongate scraper body being connected to the first end transverse to the elongate connector body, the second end having at least one resilient arm that includes a locking prong extending radially outward from the at least one resilient arm;

a toothbrush comprising an elongate toothbrush body that defines an elongate inner chamber shaped to receive the second end of the elongate connector body via a chamber aperture, the elongate toothbrush body having a proximal end and a distal end, locking apertures through the elongate toothbrush body, and a plurality of brushes extending from the proximal end;

the elongate connector body of the tongue scraper being telescopically engaged with the elongate toothbrush body of the toothbrush, so that the tongue scraper can move between a collapsed configuration and an extended configuration relative to the toothbrush; and a resilient wall covering and sealing each of the locking apertures so that when the at least one locking prong engages one of the locking apertures, the locking prong may be disengaged from the locking aperture by pressing inwardly on the resilient wall.

\* \* \* \* \*